United States Patent [19]

Feldman et al.

[11] Patent Number: 5,214,148
[45] Date of Patent: May 25, 1993

[54] ANALGESIC N-PHENYL-N-(3-OR$_1$-3-ME-4-PIPERIDINYL)AMIDES

[75] Inventors: Paul L. Feldman; Marcus F. Brackeen, both of Durham, N.C.

[73] Assignee: Glaxo Inc., Research Triangle Park, N.C.

[21] Appl. No.: 908,685

[22] Filed: Jul. 2, 1992

Related U.S. Application Data

[62] Division of Ser. No. 629,543, Dec. 18, 1990, Pat. No. 5,130,321.

[51] Int. Cl.$^5$ .................. A61K 31/445; C07D 333/06
[52] U.S. Cl. .................... 546/221; 546/210; 546/213; 546/227
[58] Field of Search ................. 514/326, 327; 546/210, 546/213, 221, 227

[56] References Cited

U.S. PATENT DOCUMENTS

| | | | |
|---|---|---|---|
| 3,124,586 | 3/1964 | Zenitz | 546/221 |
| 3,164,600 | 1/1965 | Janssen et al. | 260/293.4 |
| 3,998,834 | 12/1976 | Janssen et al. | 260/293.68 |
| 4,167,574 | 9/1979 | Janssens | 546/224 |
| 4,179,569 | 12/1979 | Janssen et al. | 546/223 |
| 4,250,184 | 2/1981 | Grier et al. | 514/327 |
| 4,584,303 | 4/1986 | Huang et al. | 546/224 |
| 4,962,115 | 10/1990 | Van Daele | 546/224 |
| 5,019,583 | 5/1991 | Feldman et al. | 514/327 |

FOREIGN PATENT DOCUMENTS 0383579 2/1990 European Pat. Off.

OTHER PUBLICATIONS

N. Lalinde et al.: *Abstr. Pap. Am. Chem. Soc.* (197 Meet., MEDI 31, 1989).

D. B. Sruleirtch et al.: QSAR: Quantitative Structure-Activity Relationships in Drug Design, pp. 377-381.

*Primary Examiner*—Richard L. Raymond
*Assistant Examiner*—Peter G. O'Sullivan
*Attorney, Agent, or Firm*—Salvatore R. Conte

[57] ABSTRACT

N-Phenyl-N-(4-piperdinyl)amide derivatives are disclosed having the general formula (I):

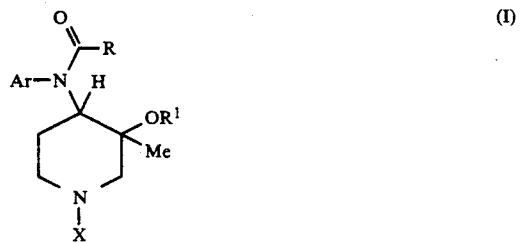

wherein X, Ar, R and R$^1$ are defined, including isomeric forms thereof and acid addition salts thereof. The compounds exhibit analgesic activity. The invention embraces the compounds (I), pharmaceutical compositions of (I) and methods of providing analgesia with (I). Also included are certain novel intermediates for making (I).

12 Claims, No Drawings

ANALGESIC N-PHENYL-N-(3-OR₁-3-ME-4-PIPERIDINYL)AMIDES

This is a division of U.S. Ser. No. 07/629,543, filed Dec. 18, 1990, now U.S. Pat. No. 5,130,321.

BACKGROUND OF THE INVENTION

The invention pertains to the field of N-phenyl-N-(4-piperidinyl)amides having potent analgesic activity. A number of patents disclose certain N-phenyl-N-(4-piperidinyl)amides having analgesic activity such as, for example, U.S. Pat. Nos. 3,164,600; 3,998,834; 4,179,569; 4,584,303; and 4,167,574. The analgesic compounds of this invention differ structurally from the prior art compounds, for example, by di-substitution in the 3-position of the piperidine ring with both an OR and a methyl substituent, wherein said $OR^1$ is hydroxy or straight chained lower alkoxy.

European patent application EP 309,043 (Van Daele et al.) discloses mono-substitution by a hydroxy or lower alkoxy in the 3-position of the piperidine ring. Not only is di-substitution in this position not disclosed, but significant structural variances at other positions are indicated and, furthermore, the compounds are non-analgesics. Mono-substitution in the 3-position is also shown with a methoxy substituent by N. Lalinde et al., Abstr. Pap. Am. Chem. Soc. (197 Meet., MEDI 31, 1989), and with a methyl substituent in European patent application EP 383,579.

The invention also provides certain novel synthetic intermediates for making formula (I) compounds.

DETAILED DESCRIPTION OF THE INVENTION

The invention relates to novel chemical compounds and pharmaceutical compositions and method of use thereof. More particularly, the subject chemical compounds are N-aryl-N-(3-$OR^1$-3-Me-4-piperidinyl)amides represented by the formula:

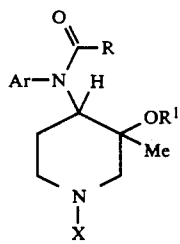

(I)

wherein:
X is a member selected from Group I consisting of:
alkoxy-carbonyl-lower alkyl (preferred), lower alkyl-carbonyloxy-lower alkyl, alkenyloxy-carbonyl-lower alkyl, and ($C_{1-2}$)alkoxy-($C_{1-2}$)alkoxy-carbonyl-lower alkyl;
and from Group II consisting of:
lower alkyl, lower alkenyl, lower alkynyl, thienyl lower alkyl, aryl lower alkyl and (4,5-dihydro-5-oxo-1H-tetrazol-1-yl) lower alkyl which can be substituted in the 4-position with lower alkyl, cyclo($C_{5-6}$) lower alkyl or aryl lower alkyl;
Ar is aryl;
R is a member selected from the group consisting of lower alkyl, preferably ethyl, and lower alkoxy-lower alkyl, preferably methoxymethyl; and
$R^1$ is a member selected from the group consisting of hydrogen and straight chained lower alkyl;
and the optically active and cis-trans isomers thereof, and the acid addition salts, preferably the pharmaceutically acceptable acid addition salts, of said compounds and isomers.

An additional aspect of the subject invention relates to certain novel intermediates which are useful in the synthesis of certain formula (I) compounds. Said intermediates are represented by formula (A) wherein Z is a benzyloxy carbonyl substituent on the ring nitrogen, replacing the aforementioned X-substituent in formula (I):

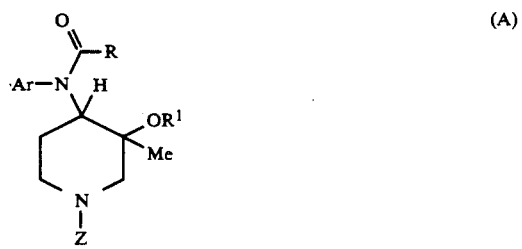

(A)

As used in the foregoing definitions the term "lower" is meant to modify the so-indicated group by 1 to 4 carbons; the unmodified terms "alkoxy" and "alkenyl" are each meant to denote straight and branch chained hydrocarbons of from 1 to about 10 carbons and include the respective "lower" group of 1 to 4 carbons; the term "halo" is generic to halogens of atomic weight less than 127, i.e. fluoro (preferred), chloro, bromo, and iodo; and the term "aryl" denotes phenyl (preferred) and mono-, di- and tri-substituted phenyl, preferably mono-substituted in the 2-position, wherein each substituent is independently selected from the group consisting of halo, lower alkyl, lower alkoxy and trifluoromethyl.

The formula (I) compounds of the invention are potent analgesics. The marked potency provided by the compounds of this invention are highly desireable in circumstances where severe pain must be eliminated, e.g. anesthesiology. The compounds of the invention can be used together with a pharmaceutically acceptable carrier to provide pharmaceutical compositions and can be administered to mammals such as man in amounts sufficient to provide analgesic effects.

The formula (I) compounds may be converted to the therapeutically active acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, hydroxyacetic, α-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxy-benzeneacetic, methanesulfonic, ethanesulfonic, benzenesulfonic, 4-methylbenzenesulfonic, cyclohexanesulfamic, α-hydroxybenzoic, 4-amino-2-hydroxybenzoic and the like acids. Conversely, the salt form can be converted by treatment with alkali into the free base form. In addition, the salt forms may be useful in the preparation of other salt forms, for example, as intermediates for conversion into the preferred pharmaceutically acceptable salt derivatives. Furthermore, the particular salt may exist as a solvate, e.g., a hydrate or a hemihydrate.

All of the compounds of formula (I) have two or more asymmetric carbon atoms in their structure and consequently they exist in the form of different optical isomeric forms or mixtures e.g., racemates, of such forms. Enantiomeric forms and mixtures of such forms may be obtained separately by the application of methods of resolution known to those skilled in the art such as, for example, salt formation with an optically active acid followed by selective crystallization.

The relative position of the $OR^1$ and Me substituents with respect to the substituents in the 4-position of the piperidine ring is designated by using the prefixes cis or trans-, according to the rules of nomenclature described in "Naming and Indexing of Chemical Substances for C.A. during the Ninth Collective Period (1972-1976) p. 861." Compounds of formula (I) having the cis or trans- configuration, essentially free of the other, may be obtained, for example, by starting their preparation from pure cis- or trans- isomers of the appropriate precursors. Substantially pure forms of the cis- and trans- isomer of compounds of formula (I) may be obtained, substantially free of the other isomer, by separating a mixture of such appropriate precursor forms by silica gel chromatography or selective crystallization.

Cis- and trans- forms may in turn be further resolved into their optical enantiomers, each essentially free of its optical counterpart, by the application of art-known methodologies such as noted previously.

All racemic and isomeric forms of the compounds of formula (I), including diastereomeric mixtures, pure diastereomers and enantiomers, and mixtures thereof, are intended to be within the scope of this invention.

The compounds of formula (I) may generally be prepared by introducing the X substituent on to the piperidine ring nitrogen of an intermediate of formula (II):

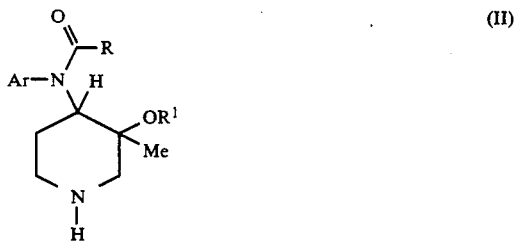

(II)

wherein Ar, R and $R^1$ are as previously defined, by the application of conventional methodologies known in the art. See, for example, EP 383,579, incorporated herein by reference thereto, for synthetic procedures suitable for the preparation of those formula (I) compounds wherein X is a member selected from Group I; and U.S. Pat. Nos. 3,998,834, 4,179,569 and 4,584,303, incorporated herein by reference thereto, for synthetic procedures suitable for the preparation of those o formula (I) compounds wherein X is a member selected from Group II.

The formula (II) intermediates are deemed to be novel and, as such, they constitute an additional aspect of this invention. As with the formula (I) compounds, due to the substituents in the 3- and 4-positions, similar different isomeric forms are possible and separately obtainable by methods known to those skilled in the art. Accordingly, all racemic and isomeric forms of the intermediate compounds of formula (II) are intended to be within the scope of this invention.

In general, the introduction of the particular X group on to the piperidine ring nitrogen of (II) is typically and conveniently carried out according to known procedures, for example, by the alkylation reaction of the piperidine nitrogen of (II) with an appropriate reactive ester of the formula "X—Y", wherein X is as previously defined and Y is a leaving group, such as, for example, halo, e.g., bromo (preferred), chloro and iodo or another reactive ester residue such as, for example, methanesulfonyl (mesyl), 4-methylbenzenesulfonyl (tosyl) and the like.

The reaction of (II) with X—Y is conveniently conducted in an inert organic solvent such as, for example, acetonitrile (preferred), an aromatic hydrocarbon, e.g., benzene, methylbenzene, dimethylbenzene and the like; a lower alkanol, e.g., methanol, ethanol, 1-butanol and the like; a ketone, e.g., 4-methyl-2-pentanone and the like; an ether, e.g., 1,4-dioxane, tetrahydrofuran (THF), 1,1-oxybisethane and the like; N,N-dimethyl-formamide (DMF); nitrobenzene; and the like. The addition of an appropriate base such as, for example, an alkali metal carbonate or bicarbonate, preferably potassium carbonate, may be utilized to neutralize the acid that is liberated during the course of the reaction. In some circumstances, the addition of an iodide salt, preferably an alkali metal iodide such as sodium iodide, is appropriate. Ambient temperatures (22°-25° C.) are generally sufficient, although somewhat higher temperatures may be employed to enhance the rate of the reaction.

In EP 383,579 (of which the inventors of this invention are also co-inventors), alternative methods are described for introducing the X substituent on to the piperidine ring nitrogen wherein X is a member of the aforementioned Group I. Such alternative methods, incorporated herein by reference to said EP 383,579, are the teachings depicted by synthetic Schemes II through VI and related examples in EP 383,579. Said methods, which are described in the hereafter quoted material from EP 383,579, may also be followed to prepare the formula (I) compounds of this invention with an X substituent of Group I except that the previously described N unsubstituted 3-disubstituted intermediates of formula (II) are utilized as the starting material. Symbols referred to in the following quoted material are defined in EP 383,579.

BEGINNING OF QUOTE FROM EP 383,579

"When X is alkoxy-carbonyl-ethyl, wherein the ethyl may be substituted with 1 or 2 $C_{1-2}$ alkyl groups for a total of 2-4 carbons, an alternative method of introducing this group on to the ring nitrogen of (II) to yield (V) is by way of a conjugate addition reaction between (II) and an α, β-unsaturated carbonyl reactant of formula (IV) in an inert organic solvent such as, for example, acetonitrile, a lower alkanol, e.g., methanol, ethanol and the like, an ether, e.g., diethyl ether, dioxane and the like; and an aromatic hydrocarbon, e.g., benzene, toluene and the like as shown, for example, in Scheme II."

[Refer to Scheme II in EP 383,579]

"When X is alkoxy-carbonyl-loweralkyl in (I-a) or alkenyloxy-carbonyl-loweralkyl in (I-c), an alternative method of introducing said X-substituent onto the piperidine nitrogen is by esterification of the corresponding acidic formula (A) compounds, i.e., formula (I) wherein X is carboxy-loweralkyl such as (VI), using the appropriate alkyl or alkenyl N,N-diisopropylpseudourea in an organic solvent, for example, chloroform, at ambient to reflux temperatures. The acids of formula (A), e.g. where $X_a$ is a carboxyethyl thus defining (VI), are believed to be novel intermediates, may be obtained by reacting (II) with an appropriate t-butyl ester of formula (III) or tertiary butyl acrylate (Michael Reaction) followed by reacting the thus-obtained product, e.g. (VII), with excess trifluoroacetic acid at 0° C. to ambient temperatures according to the following Scheme III."

[Refer to Scheme III in EP 383,579]

"The ester $CH_2$=CHCOO-tBu in Scheme III may be substituted by other esters e.g. of the formula $R^4R^5C$=$CR^6COO$-tBu where $R^4$, $R^5$ and $R^6$ are hydrogen methyl or ethyl provided that the total carbons in $R^4$, $R^5$ and $R^6$ is 0–2, to yield other acids of Formula (A)."

[Refer to Formula (A) in EP 383,579]

"Alternatively, the appropriate carboxy loweralkyl halide or acrylic acid, the acrylic acid embodiment being shown below, can be esterified with the appropriate alkyl or alkenyl-N,N-diisopropylpseudourea, for example, in chloroform at ambient to reflux temperatures, to yield the corresponding formula (III) halide ester or acrylic ester which is then introduced onto the ring nitrogen of a formula (II) compound by means of the previously mentioned alkylation reaction or conjugate addition Michael reaction, as shown in Scheme IV."

[Refer to Scheme IV in EP 383,579]

"In both Scheme III and IV, when $R^3$ is alkenyl, the double bond is not directly attached to the oxygen of the $OR^3$. In addition, the $CH_2$=CH—COOH starting material may be substituted by $R^4R^5C$=$CR^6COOH$ wherein $R^4$, $R^5$ and $R^6$ are as defined above. An alternative method of preparing the formula (I) compounds wherein X is loweralkylcarbonyloxy-loweralkyl and $R^1$ is hydrogen or methoxymethyl is by reduction of the corresponding ester (I-a) to the corresponding alcohol (VIII), for example, by conventional lithium aluminum hydride reduction in ether solution, preferably THF, at ambient temperatures. The thus-obtained alcohol (VIII) is then transformed into the reverse ester (IX) by reaction with an appropriate loweralkyl anhydride, for example, acetic acid anhydride, propionic acid anhydride, and the like, in an organic solvent such as pyridine. This is shown in the following Scheme V wherein X is in formula (I-a) is loweralkyl-$CO_2$-loweralkyl."

[Refer to Scheme V in EP 383,579]

"When X is $C_{1-2}$ alkoxy-$C_{1-2}$ alkoxy-carbonylethyl, wherein the ethyl may be substituted with 1 or 2 $C_{1-2}$ alkyl groups for a total of 2–4 carbons, the introduction of this group on to the ring nitrogen of (II) may conveniently be carried out by the reaction of (II) with an $\alpha,\beta$-unsaturated carbonyl reactant of formula (X) according to standard Michael Reaction conditions and solvents, acetonitrile being preferred, to yield the corresponding N-substituted product (V-a) as shown in Scheme VI."

[Refer to Scheme VI in EP 383,579]

"The compounds of formula (X) having a $C_{1-2}$ alkoxymethoxy-carbonyl-ethyl function are obtained by the reaction of acrylic acid with an appropriate dialkoxyalkane such as dimethoxymethane and diethoxymethane in the presence of phosphorous pentoxide. The acrylic acid may be substituted by other acids of the formula $R^4R^5C$=$CR^6COOH$ to yield other products within the invention. The compounds of formula (X) having a $C_{1-2}$ alkoxy-ethoxy-carbonylloweralkyl function are available from commercial suppliers."

END OF QUOTE FROM EP 383,579

The preparation of compounds of formula (II) begin with the known piperidines (III).

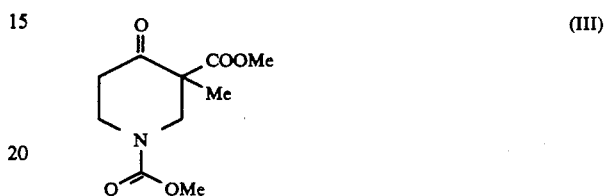

which are prepared according to the procedures published by Burke, Jr., T. R. et al., J. Med. Chem. 1986, 29, 1087 and Van Beaver, W. F. M. et al., J. Med. Chem. 1974, 17, 1047.

Reaction of compound (III) with a hydrohalic acid (hydrobromic acid preferred) at elevated temperatures (about 80° C. to reflux) for about two to ten hours yields compounds of formula (IV) in about 90–100% yield. Protection of the piperidine nitrogen with a readily removable carbamate (benzyloxycarbonyl preferred) using Schotten-Bauman conditions (base, ether, water, Z-Cl wherein Z=benzyloxycarbonyl) at about 0° C. to ambient temperature (about 20°–25° C.) for 30 min. to 5 h affords the N-benzyloxycarbonyl-3-Me-4-piperidinone of formula (V) in about 80–100% yield. Generation of the thermodynamic trimethylsilyl enol ether of formula (VI) is readily accomplished using the literature procedure of Miller, Synthesis, 1979, 730. Accordingly, the compound of formula (V) is treated with hexamethyl disilazane, $(Me_3Si)_2NH$, and trimethylsilyl iodide (TMSI) in a nonpolar organic solvent (hexanes preferred) at about 0° C. to ambient temperature to yield about 75–90% of the enol ether, N benzyloxycarbonyl-$\Delta^3$-3-methyl-4-trimethylsilyloxy-piperidinone (VI). Oxidation of (VI) to the alpha hydroxy ketone of formula (VIII) may be accomplished using the method of Rubottom, G. M. et al., Tetrahedron Lett. 1974, 4319. Accordingly, the compound of formula (VI) is reacted with the oxidant, m-chloroperoxybenzoic acid (m-CPBA), in an aprotic inert organic solvent such as, for example, hexanes, a halogenated solvent such as chloroform or methylene dichloride, and the like, in the presence of a salt such as sodium phosphate dibasic at about 0° C. to 30° C. for about 30 min to 2 h to yield N-benzylloxycarbonyl-3-methyl-3-trimethylsilyloxy-4-piperidinone of formula (VII), which need not be purified, but rather can be protodesilylated directly using strong aqueous hydrohalic acid (hydrochloric acid preferred) in an ethereal solvent such as, for example, THF (preferred), 1,4-dioxane, diethyl ether and the like, to yield the N-benzyloxycarbonyl-3-OH-3-Me-4-piperidinone of formula (VIII) in about 40–60% yields. These reactions are depicted in Scheme 1.

Scheme 1:

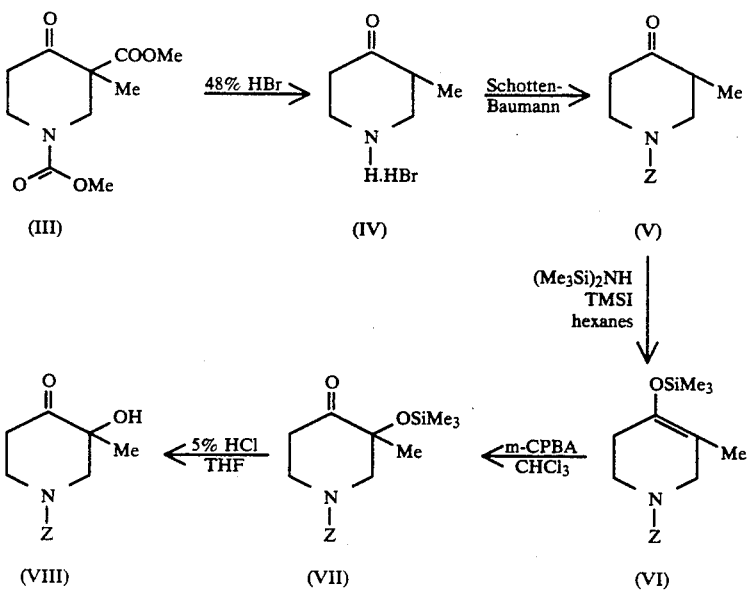

Incorporation of the 4-arylamino substitutent to generate the 4-arylimino compounds of formula (IX) is accomplished by refluxing a solution of (VIII) with an appropriate aryl amine of the formula ArNH$_2$, wherein Ar is as previously defined, and a strong acid catalyst such as an aryl sulfonic acid, for example, p-toluene-sulfonic acid monohydrate, using a Dean Stark apparatus to allow ready removal of the water formed. Reduction of the resultant 4-arylimino compounds (IX) with a hydride reducing agent (sodium borohydride preferred) in an alcoholic solution (isopropyl alcohol preferred) yields the racemic mixture of cis- and trans-isomers of the 4-arylamino compounds of formula (X) in about 40-60% overall yield from the starting compound (VIII). The diastereomeric cis- and trans-isomers (X) are readily separated from each other, for example, by using silica gel chromatography. The racemic mixture or the individual substantially pure isomers may then be independently converted into the target compounds of formula (I). Reacting (X)-cis or (X)-trans with a lower alkanoyl chloride (propionyl chloride preferred) in a polar aprotic solvent (acetonitrile preferred) with an appropriate 4-dialkylaminopyridine as a catalyst at about 60° C. to reflux temperature for about 30 min to 2 h yields the corresponding (XI)-cis or (XI)-trans compound, respectively, in predominately 40-60% yield. Subsequent removal of the piperidine nitrogen protecting group (Z=benzyloxycarbonyl), for example, by using standard hydrogenolytic conditions, such as 10% Pd/C in a lower alkanol with gaseous hydrogen yields the corresponding cis- and trans-compounds of formula (II) wherein Ar and R are as previously defined and R$^1$ is hydroxy. These reactions are depicted in Scheme 2.

Scheme 2:

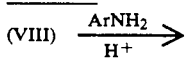

-continued
Scheme 2:

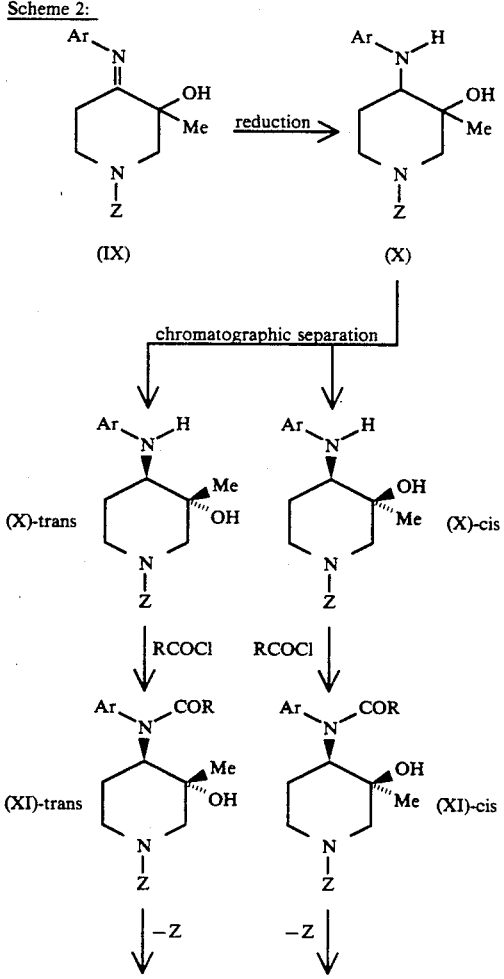

Scheme 2:
-continued

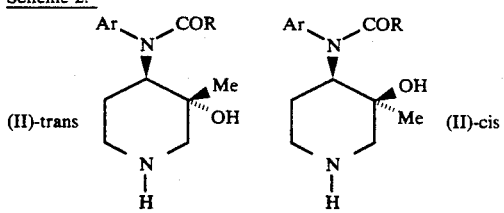

Synthesis of the formula (II) compounds, in which the hydroxy function in the 3-position is converted to a straight chained lower alkoxy function, is accomplished by first alkylating the hydroxyl group of the formula (XI) compounds, as either the enantiomerically pure cis or trans diastereomers or as the racemates, using an alkali metal hydride (sodium hydride preferred) in an ethereal solvent (preferably THF enhanced by the addition of acetonitrile) to deprotonate the hydroxyl group followed by addition of a straight chained lower alkyl iodide (methyl iodide preferred). The resultant 3-lower alkoxy compounds of formula (XII) are then acylated with the appropriate RCOCl acylating agent as previously described to yield the corresponding compounds of formula (XIII). Hydrogenolysis of (XIII) affords removal of the nitrogen protecting group (Z) to yield compounds of formula (II) in which Ar and R are as previously described. These reactions are depicted in Scheme 3.

Scheme 3:

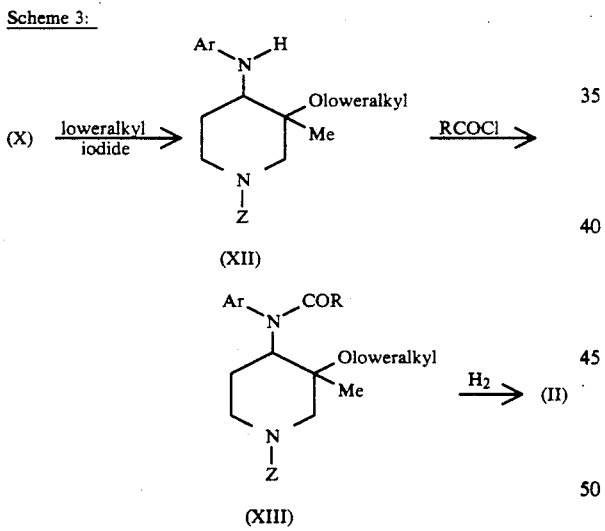

Determination of the relative stereochemistry of the vicinal substituents on the 3- and 4- positions of the piperidine ring in the compound of formula (X) is accomplished by synthesizing (X)-trans wherein Ar is phenyl, R is ethyl and $R^1$ is hydrogen, using an unambiguous synthetic route and then analyzing the mixture of cis- and trans- isomers obtained in reducing (IX) to see which isomer matched (X)-trans. The synthetic route used to obtain substantially pure (X)-trans begins with the known piperidine of formula (XIV). Reduction of (XIV) to (XV), for example, by using sodium borohydride in methanol, followed by mesylation and elimination of methane sulfonic acid generates compound (XVI). Reduction of the ester (XVI) yields allylic alcohol (XVII) which is readily converted to the epoxy mesylate (XVIII) via m-CPBA oxidation and mesylation. Reaction of (XVIII) with the dimethylaluminum amide of aniline in toluene at 0° C. followed by basic hydrolysis of the aluminum alkoxide yields epoxide (XIX) in 20–40% yield. Reduction of the epoxide with LiEt$_3$BH in tetrahydrofuran yields (X)-trans, which exactly matched one of the isomers obtained in the reduction of (IX) by sodium borohydride as depicted in Scheme 2. The stereochemistry of (X)-trans obtained in the latter route was assigned by virtue of the necessary trans opening of epoxide (XVIII) with the aluminum amide nucleophile. The precedent for this reaction can be found in Overman, L. E., Flippin, L. A. Tetrahedron Lett. 1981, 22, 195. These reactions are depicted in Scheme 4.

Scheme 4:

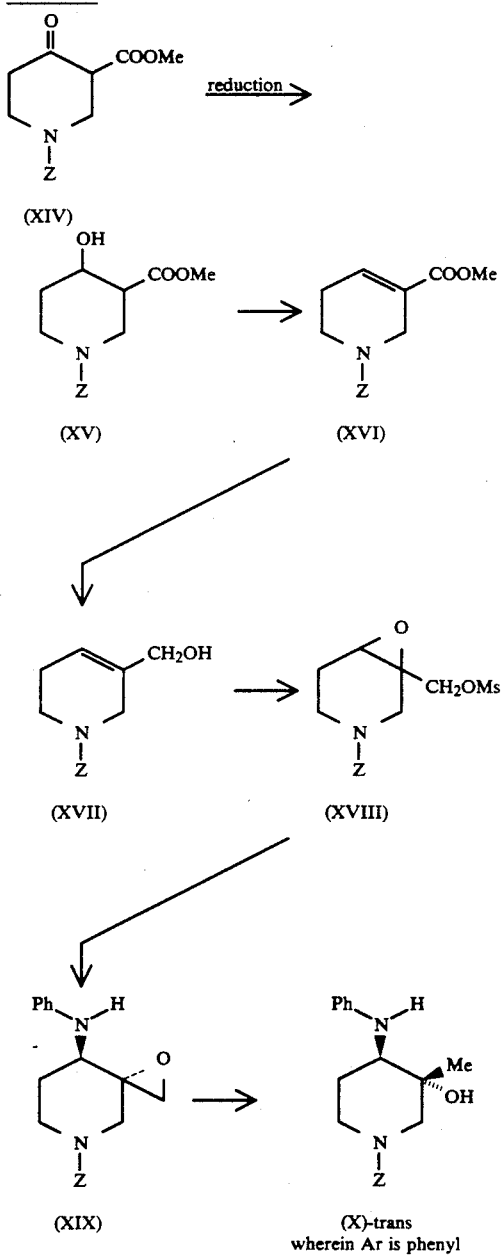

Typical compounds of formula (I) include the cis and trans diastereomers of:

2-[3-OH-3-Me-4-[(1-oxopropyl)phenylamino]-piperidine]ethyl acetate HCl;

3-[3-OH-3-Me-4-[(1-oxopropyl)phenylamino]-piperidine]propanoic acid, ethoxymethyl ester HCl;

3-[3-OMe-3-Me-4-[(1-oxopropyl)phenylamino]-piperidine]propanoic acid, allyl ester oxalate;

3-[3-OH-3-Me-4-[(1-oxopropyl)-2-fluorophenylamino]-1-piperidine]propanoic acid, methyl ester HBr;

2-[3-OMe-3-Me-4-[(1-oxopropyl)-2-fluorophenylamino]-1-piperidine]ethanoic acid, 3-butenyl ester acetate;

N-Ethyl 3-OH-3-Me-4-[(1-oxoethyl)phenylamino]-1-piperidine HCl;

N-Allyl-3-OH-3-Me-4-[(1-oxoethyl)phenylamino]-1-piperidine HCl;

N-[(4,5-Dihydro-5-oxo-1H-tetrazolyl-1-yl)ethyl]-3-OH-3-Me-4-[(1-oxoethyl)phenylamino]-1 piperidine oxalate; and N-Propargyl-3-OH-3-Me-4-[(1-oxoethyl)phenylamino]-1-piperidine HCl The compounds of formula (I) and the isomeric forms and pharmaceutically acceptable acid addition salts thereof are useful analgesics, as demonstrated, for example, in experimental animals. Typical of the in vitro and in vivo testing procedures for analgesic activity are the guinea pig ileum assay and the rat tail withdrawal assay, respectively.

A. Guinea Pig Ileum Assay (in vitro):

Compounds are tested for opioid activity in the isolated guinea pig ileum using the method of Kosterlitz, H. W. and Watt, A. J., Br. J. Pharmacol. 33:266–276 (1968) with modifications found in James, M. K. and Leighton, H. J., J. Pharmacol Exp. Ther. 240:138–144 (1987). The terminal ileum is removed from male Hartley guinea pigs after sacrifice by cervical dislocation. The isolatd ileum is washed and placed in Krebs-Henseleit buffer oxygenated with 95% $O_2$ and 5% $CO_2$ mixture and maintained at 37° C. The washed ileum is cut into segments (2.0–2.5 cm) and mounted on platinum ring electrodes. The ileal segments are then placed in 10 mL temperature-controlled tissue baths containing oxygenated Krebs-Henseleit buffer is as follows (millimolar): NaCl, 118.1; KCl, 4.15; $CaCl_2$, 2.5; $MgSO_4$, 1.2; $KH_2PO_4$, 1.23; $NaHCO_3$, 25.5 and glucose, 11.1.

The ileal segments are stimulated at 0.1 Hertz, 0.5 milliseconds duration at a supramaximal voltage to induce contractions. Opioid activity in the test compounds is manifested as inhibition of electrically evoked contractions. A non-cumulative concentration-effect curve for each test compound is performed to assess the ability of the compound to inhibit contraction in the guinea pig ileum.

After the concentration-effect curve is completed, naloxone is added to the tissue baths to determine if the compound-induced inhibition of contraction is reversed. Antagonism of the inhibition by naloxone confirms that the inhibitory effects of the compounds are mediated through opioid receptors. Assay results are expressed as $EC_{50}$ values (a measure of potency), defined as the concentration producing fifty percent of the maximal response, and is expressed in molar units (moles of compound/liter).

B. Rat Tail Withdrawal Assay (in vivo)

The analgesic efficacy of test compounds are evaluated in a rat tail withdrawal reflex model modified form D'Amour, F. E. and Smith, D. L., J. Pharmacol. Exp. Ther. 72:74–79 (1941). Male Sprague-Dawley rats are anesthetized and implanted with femoral vein cannulae and allowed to recover overnight. After recovery, the test compounds are administered intravenously through the cannula and effects of tail withdrawal latency are measured. Tail withdrawal latency is measured as the time to tail movement by the rat after exposure of the tail to a radiant heat source. The heat source is calibrated to produce a temperature of 62° C. after 15 seconds. Tail withdrawal latency in the absence of drugs is six to eight seconds. Test compounds demonstrating analgesic activity prolong tail withdrawal latency beyond that seen in the absence of drugs. A maximal latency cut-off of fifteen seconds is imposed to prevent tissue damage. The assay is verified with known opioids as standards. Results of these studies are expressed as $ED_{50}$ values, calculated as the dose producing a tail withdrawal latency equal to half the difference between the maximum latency (15 seconds) and the baseline latency (six to eight seconds). $ED_{50}$ values are expressed as milligrams of compound/kilogram of body weight. Duration of action is defined as the time (in minutes) necessary for the tail withdrawal response to return to baseline values after being elevated in response to drug administration. Duration of action is measured at the lowest dose producing a fifteen second (maximum) tail withdrawal latency.

In Table I, test results obtained from the aforementioned guinea pig ileum assay A and B rat tail withdrawal assay B are listed for the indicated compounds of formula (I). Said results are not given for the purpose of limited the invention to said compounds but to exemplify the analgesic activity of all compounds within the scope of formula (I). For comparison purposes, test results obtained for three well known 4-anilidopiperidine analgesics, fentanyl, sufentanil and alfentanil, are also listed.

TABLE I

Test Compound:
  A. Trans-N-[1-(2-thienyl)ethyl]-3-hydroxy-3-methyl-4-[(1-oxopropyl)phenylamino]piperidine oxalate;
  B. Cis-N-(1-phenethyl)-3-hydroxy-3-methyl-4-[(1-oxopropyl)phenylamino]piperidine oxalate;

| Test Compound | Assay A $EC_{50}$ (molar) | Assay B $ED_{50}$ (mg/kg) | Duration of Action (min) |
|---|---|---|---|
| A | $3.14 \times 10^{-8}$ | 0.12 | 20 |
| B | $4.72 \times 10^{-8}$ | >3.0 | — |
| C | $1.03 \times 10^{-8}$ | $5.6 \times 10^{-3}$ | 60 |
| D | $2.22 \times 10^{-6}$ | >3.0 | — |
| E | $1.11 \times 10^{-6}$ | 0.17 | 70 |
| F | $7.08 \times 10^{-6}$ | 0.11 | 40 |
| G | $3.07 \times 10^{-6}$ | >3.0 | — |
| H | $1.22 \times 10^{-10}$ | $5.2 \times 10^{-5}$ | 60 |
| I | $2.80 \times 10^{-10}$ | — | — |
| J | $1.90 \times 10^{-7}$ | >3.0 | — |
| K | $3.30 \times 10^{-8}$ | 0.17 | 30 |
| fentanyl | $1.76 \pm 0.36 \times 10^{-9}$ | 0.0046 | 60 |
| sufentanil | $7.43 \pm 1.53 \times 10^{-9}$ | 0.0013 | 80 |
| alfentanil | $2.01 \pm 0.12 \times 10^{-8}$ | 0.0045 | 55 |

The results in Table I illustrate that the subject compounds have opioid activity as demonstrated by naloxone-reversible inhibition of electrically evoked contraction in the guinea pig ileum.

In view of their analgesic activity, the subject compounds may be formulated into various pharmaceutical forms for administration purposes. To prepare the pharmaceutical compositions of this invention, an effective analgesic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, for example, for administration orally, transdermally, rectally or parenterally. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. For parenteral compositions, the carrier will usually comprise sterile water, at least in large part, though other ingredients, for example, to aid solubility, may be included. Injectable solutions, for example may be prepared in which the carrier comprises isotonic saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form, as used herein, refers to physically discrete units suitable as unitary dosages, each unit containing a predetermined quantity of active ingredient calculated in product the desired therapeutic effect in association with the required pharmaceutical carrier. Examples of such dosage unit forms are tablets (including scored or coated tablets), capsules, pills, powder packets, wafers, injectable solutions or suspensions, teaspoonsfuls and the like, and segregated multiples thereof.

In view of the analgesic activity of the subject compounds, it is evident that the present invention provides a method of preventing or combatting pain, that is, providing analgesia, in warm-blooded mammals, including humans, by the systemic administration of an effective analgesic amount of a compound of formula (I) or a pharmaceutically acceptable isomer or acid addition salt thereof in admixture with a pharmaceutical carrier. Although the amount of active ingredient to be administered may vary within rather wide limits, depending on the particular circumstances of the case, doses of from about 0.001 to about 10 mg/kg, and preferably from about 0.01 to about 1.0 mg/kg, administered once, repeatedly or continuously (e.g., i.v. drip), are generally found effective. The preferred route of administration is parenteral, particularly by the intravenous route.

The following examples are intended to illustrate, and not to limit the scope of the present invention.

EXAMPLE 1

3-methyl-4-piperidone hydrobromide salt

A solution of 1,3-dicarbomethoxy-3-methyl-4-piperidone (51.45 g, 225 mmol) in hydrobromic acid (48%, 250 mL) is heated under reflux for 4 h and then cooled to room temperature. The resultant solution is concentrated in vacuo to give an orange colored solid. The solid is suspended in methanol (50 mL) and concentrated in vacuo again to give 3-methyl-4-piperidone hydrobromide salt: 42.9 g; 98%; mp 203-°205° C.

EXAMPLE 2

N-benzyloxycarbonyl-3-methyl-4-piperidone

To a mechanically stirred mixture of benzylchloroformate (33.1 mL, 232 mmol, 105 mol %), sodium bicarbonate (37.2 g, 442 mmol, 200 mol %), ether (250 mL), and water (250 mL) is added;3-methyl-4-piperidone hydrobromide salt (42.9 g, 221 mmol) in portions over 10 min. The resultant mixture is stirred for 2 h and the organic phase separated. The aqueous phase is extracted with ether ($2 \times 150$ ml) and the combined organics dried ($MgSO_4$), filtered, and concentrated to an oily residue. This residue crystallized on standing at 23° C. and was recrystallized from hexanes/ethyl acetate to give N-benzyloxycarbonyl-3-methyl-4-piperidone as a solid: 51.2 g; 93%; mp 33°-35° C.

EXAMPLE 3

N-benzyloxycarbonyl-$\Delta^3$-3-methyl-4-trimethylsilyloxy piperidine

A stirred solution of N-benzyloxycarbonyl-3-methyl-4-piperidone (20.0 g, 81 mmol) and hexamethyl disilizane (26.15 g, 162 mmol, 200 mol %) in hexanes (500 ml) is chilled to 0° C. and trimethylsilyl iodide (25.0 g, 125 mmol, 154 mol %) is added in one portion. The resultant suspension is stirred at 0° C. for 30 min and then warmed to 23° C. whereupon stirring is continued for 4.5 h. The suspension is then filtered and the filtrate washed with a sodium hydroxide solution (2N, 200 mL). The organic phase is then separated and dried ($MgSO_4$), filtered, concentrated, and chromatographed on silica gel (89% hexanes, 10% ethyl acetate, 1% triethylamine) to give N-benzyloxycarbonyl-$\Delta^3$-3-methyl-4-trimethylsilyloxy piperidine as an oil: 21.62 g; 84%.

EXAMPLE 4

Cis- and trans-N-benzyloxycarbonyl-4-anilino-3-hydroxy-3-methyl piperidine

To a stirred suspension of 90% m-CPBA (25.42 g, 133 mmol, 196 mol %) in hexanes (500 mL) at 23° C. is added N-benzyloxocarbonyl-$\Delta^3$-3-methyl-4-trimethylsilyloxy piperidine (21.69 gms, 67.9 mmol), and sodium phosphate dibasic (20.0 g, 141 mmol, 207 mol %). The suspension is stirred for 2 h and the m-chlorobenzoic acid is filtered off. The filtrate is then washed with a saturated sodium thiosulfate solution (250 mL), dried ($MgSO_4$), filtered, and concentrated to give crude N-benzyloxycarbonyl-3-methyl-3-trimethylsilyloxy-4-piperidone as an oily residue: 22.0 g, crude yield (97%).

The thus-obtained N-benzyloxycarbonyl-3-methyl-3-trimethylsilyloxy-4-piperidone is dissolved in THF (450 mL) and concentrated hydrochloric acid (50 mL) is added. The resultant solution is stirred at 23° C. for 24 h and concentrated to an oily residue. The residue is suspended in a saturated sodium bicarbonate solution (250 mL) and the resultant suspension is extracted with ether ($2 \times 100$ mL). The organics are combined, dried ($MgSO_4$), filtered and concentrated to give crude N-benzyloxycarbonyl- 3 -hydroxy-3-methyl-4-piperidone as an oil: 17.2 g.

The thus-obtained N-benzyloxycarbonyl-3-OH-3-Me-4-piperidone (17.2 g, 65.4 mmol) and aniline (7.61 g, 81.7 mmol, 125 mol %), are dissolved in toluene (250 mL) and the solution is heated under reflux (using a Dean Stark apparatus to remove water formed during the reaction) with p-toluene-sulfonic acid monohydrate (1.0 g, 5.25 mmol, 8 mol %) for 2 h and cooled to 23° C. The red colored solution is concentrated to an oil of the 4-phenylimino derivative, N-benzyloxycarbonyl 3-OH-3-Me-4-phenylimino-4-piperidine, which is then reduced to the corresponding 4-phenylamino derivative, N-benzyloxycarbonyl-3-OH-3-Me-4-phenylamino-4-piperidine as follows.

The oily 4-phenylimino derivative is dissolved in isopropyl alcohol (200 mL) and stirred at 23° C. as sodium borohydride (4.83 g, 131 mmol, 800 mol %) is added in portions. The resultant suspension is stirred for 2 h and quenched with water (50 mL) whereupon stirring is continued for 1 h. The isopropyl alcohol is then removed in vacuo and the resultant aqueous suspension extracted with EtOAc (2×250 mL). The organics, containing the mixture of N-benzyloxycarbonyl-3-OH-3-Me-4-phenylamino-4-piperidine diastereomers, are combined, dried (MgSO)$_4$), filtered, concentrated, and chromatographed on silica gel (60% hexanes, 40% EtOAc) to give a 6:4 mixture of the corresponding cis and trans diastereomers as an oil: 15.9 g. The oily isomeric mixture is chromatographed again on silica gel (85% hexanes, 15% EtOAc) to give the pure cis diastereomer: 6.5 g, and pure trans diastereomer: 4.8 g, of N-benzyloxycarbonyl-4-anilino- 3-hydroxy-3-methyl piperidine and a smaller quantity of a mixture of both.

EXAMPLE 5

Cis-N-benzyloxycarbonyl-3-hydroxy-3-methyl-4-[(1-oxopropyl)phenylamino]piperidine A solution of cis-N-benzyloxycarbonyl-4-anilino-3-hydroxy-3-methyl piperidine (2.0 g, 5.88 mmol), propionyl chloride (5.1 mL, 58.8 mmol, 1000 mol %), and 4-dimethylaminopyridine (2.15 g, 17.6 mmol, 300 mol %), in acetonitrile (90 mL) is stirred and refluxed for 30 min. The resultant solution is cooled to 23° C. and concentrated to an oily residue which is suspended in 1M phosphoric acid solution (50 mL) and then extracted with EtOAc (3×50 mL). The combined organics are dried (MgSO$_4$), filtered, and concentrated to give a mixture of mono and bispropionylated material which is separated by chromatography on silica gel (80% hexanes, 20% EtOAc) to give the (XI)-cis diastereomer, cis-N-benzyloxycarbonyl-3-hydroxy-3-methyl-4-[(1-oxopropyl)phenylamino]piperidine, as an oil: 1.1 g, 47%.

EXAMPLE 6

Trans-N-benzyloxycarbonyl-3-hydroxy-3-methyl-4-[(1-oxopropyl)phenylamino]piperidine This compound is prepared by following the procedure described in Example 5 except that an equivalent amount of the corresponding trans-isomer of the starting piperidine is utilized.

EXAMPLE 7

Cis-3-hydroxy-3-methyl-4-[(1-oxopropyl)-phenylamino]piperidine

A suspension of cis-N-benzyloxycarbonyl-3-hydroxy-3-methyl-4-[(1-oxopropyl)phenylamino]-piperidine (1.1 g, 2.77 mmol) in methanol (10 mL) and 10% Pd/C (100mg) is stirred at 23° C. under 1 atm of hydrogen for 16 h and then filtered through a bed of celite. The filtrate is concentrated to give cis-3-hydroxy-3-methyl-4-[(1-oxopropyl)phenylamino]-piperidine as an oil: 690 mg, 95%

EXAMPLE 8

Trans-3-hydroxy-3 methyl-4-(1-oxopropyl)phenylamino]-piperidine This compound is prepared by following the procedure described in Example 7 except that an equivalent amount of the corresponding trans-isomer of the starting piperidine is utilized.

EXAMPLE 9

Cis-3-[3-hydroxy-3-methyl-4[(1-oxopropyl)-phenylamino-1-piperidine]propanoic acid, methyl ester A solution of cis-3-hydroxy-3-methyl-4-[(1-oxopropyl)-phenylamino]piperidine (350 mg, 1.33 mmol) and methyl acrylate (240µL, 2.66 mmol, 200 mol %) in methanol (6 mL) is stirred for 16 h and concentrated to an oily residue which is chromatographed on silica gel (50% hexanes, 50% EtOAc) to give cis-3-[3-hydroxy-3-methyl-4-[(1-oxopropyl)phenylamino]-1-piperidine]-propanoic acid, methyl ester as an oil: 300 mg, 65%.

Hydrochloride salt: The HCl salt is made by dissolving the free base in anhydrous ether and bubbling in dry hydrogen chloride gas. The precipitate is filtered and recrystallized from EtOAc/MeOH. mp 200°-201° C. Anal. Calcd. for $C_{19}H_{29}N_2O_4Cl$: C, 59.3; H, 7.6; N, 7.3%. Found: C, 59.3; H, 7.6; N, 7.3%.

EXAMPLE 10

Trans-3-3-hydroxy-3-methyl-4 [(1-oxopropyl)phenylamino-1-piperidine]propanoic acid, methyl ester This compound is obtained by following the procedure described in Example 9 except that an equivalent amount of the corresponding trans-isomer of the starting piperidine is lo utilized.

Hydrochloride salt: The HCl salt is made as described in Example 11. mp 184°187° C. Anal. Calcd. for $C_{19}H_{29}N_2O_4Cl$: C, 58.6; H, 7.6; N, 7.2%. Found: C, 58.6; H, 7.6; N, 7.1%.

EXAMPLE 11

Cis-N-[1-(2-thienyl)ethyl]-3-hydroxy-3-methyl-4-(1-oxopropyl)phenylamino[piperidine A mixture of cis 3-hydroxy-3-methyl 4 [(1-oxopropyl) phenylamino]piperidine (350 mg, 1.33 mmol), 2-(2-thienyl)-1-o-(4-potassium carbonate (100 mg, 0.72 mmol, 54 mol %), and sodium iodide (100 mg, 0.67 mmol, 50 mol %), in acetonitrile (5 mL) is stirred at 50° C. for 16 h and cooled to 23° C.. The mixture is then concentrated and the resultant residue dissolved in 1 phosphoric acid solution (10 mL). This solution is washed with EtOAc (2 x 10 mL) and then basified to a pH of 7.5 with a saturated sodium carbonate solution. The resultant suspension is extracted with EtOAc (3×10 mL) and the combined extracts dried(MgS04), filtered, concentrated, and chromatographed on silica gel (50% Hexanes, 50% EtOAc) to give cis-N-[1-(2-thienyl)ethyl] -3-hydroxy- 3-methyl 4 [(1 oxopropyl)-phenylamino]piperidine as an oil: 250 mg, 50%.

Hydrochloride salt: The HCl salt was made as described in example 11. mp 163°-165° C. Anal. Calcd. for $C_{21}H_{29}N_2O_2SCl$ (1/4 mole H20): C, 61.0; H, 7.1; N, 6.8%. Found: C, 61.1; H, 7.2; N, 6.8%.

EXAMPLE 12

Trans-N-1-(2-thienyl)ethyl]-3-hydroxy 3-methyl-4-[(1-oxopropyl)phenylamino]piperidine This compound is obtained by following the procedure described in Example 11 except that an equivalent amount of the corresponding trans-isomer of the starting piperidine is utilized.

Oxalate salt: The oxalate salt is made by dissolving the free base in ether and adding a solution of oxalic acid in ether. The resulting precipitate is recrystallized from EtOAc/MeOH: mp 151°–153° C. Anal. Calcd. for $C_{23}H_{30}N_2O_6S$ (1 mole $H_2O$): C, 57.5; H, 6.7; N, 5.8%. Found: C, 57.9; H, 6.5; N, 5.8%.

EXAMPLE 13

Trans-N-phenethyl 3 hydroxy 3-methyl-4-[(1-oxopropyl) phenylamino]piperidine

A mixture of trans-3-hydroxy-3-methyl-4-[(1-oxopropyl)phenylamino]piperidine (136 mg, 0.522 mmol), 2-bromoethylbenzene (100µL, 0.78 mmol, 150 mol %), potassium carbonate (144 mg, 1.04 mmol, 200 mol %), and acetonitrile (1 mL) is stirred at 23° C. for 2 days and then diluted with H20 (1 mL). The resultant suspension is extracted with EtOAc (3×2 mL) and the extracts combined, dried (MgSO_4), filtered, concentrated, and chromatographed on silica gel (75% Hexanes, 25% EtOAc) to give trans-N-phenethyl-3-hydroxy-3-methyl-4-[(1-oxopropyl) phenyl-amino]piperidine as an oil: 87 mg, 46%.

Oxalate salt: The oxalate salt is made by dissolving the free base in EtOAc and adding an etheral solution of oxalic acid. The resultant precipitate is recrystallized from EtOAc/CH_3OH to yield the oxalate salt as a fine crystalline solid. mp 163°–165° C.. Anal. Calcd. for $C_{25}H_{32}N_2O_6$: C, 64.5; H, 6.9; N, 6.0%. Found: C, 64.8; H, 7.0; N, 6.1%.

EXAMPLE 14

Cis N-phenethyl 3-hydroxy-3-methyl-4-[(1-oxoproyl)phenylamino]-piperidine

This compound is obtained by following the procedure described in Example 13 except that an equivalent amount of the corresponding cis isomer of the starting piperidine is utilized.

EXAMPLE 15

Trans-N-benzyloxocarbonyl-4-anilino 3-methoxy 3 methyl piperidine

To a stirred solution of trans-N-benzyloxycarbonyl-4-anilino-3-hydroxy-3-methyl-piperidine (2.0 g, 5.88 mmol) in THF (200 mL) and acetonitrile (50 mL) is added sodium hydride $ (1.17 gms, 29.3mmol, 500 mol %). The resultant suspension is stirred at 23° C. for 10 min and methyl iodide (1.47 mL, 23.5 mmol, 400 mol %) is added. Stirring is continued at 23° C. for 2 h and the solution is quenched with 1M phosphoric acid solution (50 mL). The mixture is then concentrated in vacuo to an aqueous suspension and extracted with ether (3×50 mL). The combined organics are dried (MgSO_4), filtered, concentrated, and chromatographed on silica gel (80% hexanes, 20% EtOAc) to give trans-N benzyloxycarbonyl-4-anilino-3-methoxy-3-methylpiperidine as an oil: 1.97 g, 95%.

EXAMPLE 16

Cis-N-benzyloxycarbonyl-4-anilino 3-methoxy-3-methyl piperidine

This compound is prepared by following the procedure described in Example 15 except that an equivalent amount of cis-N benzyloxycarbonyl-4-anilino-3-OH-3-Me-piperidine is used as the starting material.

EXAMPLE 17

Cis-N-benzyloxycarbonyl-3-methoxy-3-methyl-4-[(1-oxopropyl)-phenylamino1piperidine A solution of cis-N benzyloxycarbonyl-4 anilino 3-methoxy-3-methyl-piperidine (560 mg, 1.58 mmol), propionyl chloride (686µL, 7.89 mmol, 500 mol %), and 4-dimethylaminopyridine (578 mg 4.73 mmol, 300 mol %), in acetonitrile 7.5 mL) is stirred and refluxed for 30 min. The resultant solution is concentrated to an oily residue which is suspended in 1M phosphoric acid solution (10 mL) and extracted with EtOAc (2×10 mL). The organics were combined, washed with brine (10 mL), dried(MgSO_4), filtered, concentrated, and chromatographed on silica gel (50% EtOAc, 50% Hexanes) to give cis-N-benzyloxycarbonyl 3-methoxy-3-methyl-4-[(1 oxopropyl)phenylamino]piperidine as an oil: 473 mg, 73%.

EXAMPLE 18

Trans-N-benzyloxycarbonyl-3-methoxy-3-methyl-4-[(1-oxopropyl)phenylamino]piperidine This compound is obtained by following the procedure described in Example 17 except that an equivalent amount of the corresponding trans-isomer of the starting piperidine is utilized.

EXAMPLE 19

Cis-3-methoxy-3 methyl 4 [(1-oxoproyl1phenylamino]piperidine

A suspension of cis-N-benzyloxycarbonyl-3-methoxy-3-methyl-4-[(1-oxopropyl)phenylamino]-piperidine (473 mg, 1.15 mmol) in CH_3OH (5 mL) and 10% Pd/C (40 mg) is stirred under 1 atm of hydrogen at 23° C. for 24 h and then filtered through a bed of celite. The filtrate is concentrated to give cis-3-methoxy-3-methyl-4-[(1-oxopropyl)phenylamino]piperidine as an oil: 300 mg, 94%.

EXAMPLE 20

Trans-3-methoxyl-3-methyl-4-[(1-oxopropyl)-phenylamino]piperidine

This compound is obtained by following the procedure described in Example 19 except that an equivalent amount of the corresponding trans-isomer of the starting piperidine is utilized.

EXAMPLE 21

Cis-3-[3-methoxy-3-methyl-4-[(1-oxopropyl)-phenylamino]-1-piperidine]propanoic acid, methyl ester A solution of cis-3-methoxy-3-methyl-4-[(1-oxopropyl)phenylamino]piperidine (200 mg, 0.72 mmol), and methyl acrylate (130 mL, 1.44 mmol, 200 mol %) in methanol (3 mL) is stirred at 23° C. for 24 hours and concentrated to an oily residue which is chromatographed on silica gel (50% Hexanes, 50% EtOAc) to give cis-3-[3-methoxy-3-methyl-4-[(1-oxopropyl)

phenylamino]1-piperidine]propanoic acid, methyl ester as an oil: 223 mg, 85%.

Oxalate salt: The oxalate salt is prepared as described in Example 13. mp 156°–157° C.

EXAMPLE 22

Trans-3-[3-methoxy-3-methyl-4-[(1-oxopropyl)-phenylamino]-1-piperidine]propanoic acid, methyl ester This compound is made as described in Example 21 except the trans isomer of the starting piperidine is used.

Oxalate salt: The oxalate salt is prepared as described in Example 13: mp 154°–155° C. Anal. Calcd. for $C_{22}H_{32}N_2O_8$ (½ mole $H_2O$): C, 57.3; H, 7.2; N, 6.1%. Found: C, 57.6; H, 7.1; N, 6.0%.

EXAMPLE 23

Cis-N-1-(2-thienyl)ethyl]-3-methoxy-3-methyl-4-(1-oxopropyl)phenylamino]piperidine A mixture of cis-3-methoxy-3-methyl-4-[(1-oxopropyl)phenylamino]piperidine (150 mg, 0.54 mmol), 2-(2-thienyl-1-o-(4-methylphenylsulfonyl)ethanol (306 mg, 1.08 mmol, 200 mol %), potassium carbonate (100 mgs, 0.72 mmol, 133 mol %), and sodium iodide (50 mg, 0.33 mmol, 163 mol %) in acetonitrile (5 mL) is stirred at 23° C. for 16 h. The mixture is then diluted with $H_2O$ (10 mL) and extracted with EtOAc (2×10 mL). The combined organics are dried ($MgSO_4$), filtered, concentrated, and chromatographed on silica gel (50% Hexanes, 50% EtOAc) to give cis-N-[1-(2-thienyl) ethyl]-3-hydroxy-3-methyl-4-[(1-oxopropyl)phenylamino]-piperidine as an oil: 150 mg, 72%.

Hydrochloride salt: The HCl salt is prepared as described in Example 11: mp 240°–242° C. Anal. Calcd. for $C_{22}H_{31}N_2O_2SCl$: C, 62.1; H, 7.5; N, 6.6%. Found: C, 62.5; H, 7.4; N, 6.6%.

EXAMPLE 24

Trans-N-1-(2-thienyl)ethyl]-3-methoxy-3-methyl-4-[(1-oxopropyl)phenylamino]piperidine This compound is obtained by following the procedure described in Example 23 except that an equivalent amount of the corresponding trans-isomer of the starting piperidine is utilized.

Oxalate salt: The oxalate salt is made as described in Example 13. mp 135°–136° C. Anal. Calcd. for $C_{24}H_{32}N_2O_6S$: C, 60.5; H, 6.8; N, 5.5%. Found: C, 60.2; H, 6.7; N, 5.4%.

EXAMPLE 25

Cis-(1-phenethyl)-3-methoxy-3-methyl-4-[(1-oxopropyl)phenylamino]piperidine

A mixture of cis 3 methoxy 3 methyl 4 [(1 oxopropyl)phenylamino]piperidine (150m9, 0.54 mmol), 2-bromoethylbenzene (200 mg, 1.1 mmol, 200 mol %), potassium carbonate (100 mg, 0.72 mmol, 133 mol %), and sodium iodide (50 mg, 0.33 mmol, 61 mol %) in acetonitrile (2.0 mL) is stirred at 50° C. for 16 h and cooled to 23° C. The resultant mixture is diluted with $H_2O$ (5 mL) and extracted with EtOAc (3×10 mL). The organics are combined, dried($MgSO_4$), filtered, concentrated, and chromatographed on silica gel (50% Hexanes, 50% EtOAc) to give cis N-phenethyl-3-methoxy-3-methyl-4-[(1-oxopropyl)phenylamino]-piperidine as an oil: 177 mg, 86%.

Oxalate salt: The oxalate salt is prepared as described in

EXAMPLE 13: mp 159°–163° C. Anal. Calcd. for $C_{26}H_{32}N_2O_6$; (2 moles $H_2O$): C, 61.9; H, 7.2; N, 5.6%. Found: C, 62.2; H, 6.8; N, 5.3%.

EXAMPLE 26

Trans-N-phenethyl-3 methoxy 3-methyl-4-[(1-oxopropyl)phenylamino]piperidine

This compound is prepared by following the procedure described in Example 25 except that an equivalent amount of the corresponding trans-isomer of the starting piperidine is utilized.

Hydrochloride salt: The HCl salt is prepared as described in Example 11: mp 171°–172° C. Anal. Calcd. for $C_{24}H_{33}N_2O_2Cl$ (¼ mole $H_2O$): C, 68.4; H, 7.9; N, 6.6%. Found: C, 68.4; H, 8.0; N, 6.9%.

EXAMPLE 27

Cis-N-benzyloxycarbonyl-4-anilino-3-n-butoxy-3-methylpiperidine

The procedure of Example 15 is followed except that an equivalent amount of cis-N-benzyloxycarbonyl-4-anilino-3-OH-3-Me-piperidine is used as the starting material in place of the corresponding trans piperidine, and an equivalent amount of n-butyl iodide is used as the alkylating agent in place of methyl iodide, to yield as final product, cis-N-benzyloxycarbonyl-4-anilino-3-n-butoxy-3-methyl-piperidine.

EXAMPLE 28

Cis-N-benzyloxycarbonyl-3-n-butoxy-3-methyl-4-[(1-oxoethyl)phenylamino]piperidine The acylation procedure of Example 17 is followed except that an equivalent amount of the cis-piperidine obtained in Example 27 is utilized as the starting piperidine, and an equivalent amount of acetyl chloride is used as the acylating agent in place of propionyl chloride, to yield as final product, cis-N-benzyloxycarbonyl-3-n-butoxy-3-methyl-4-[(1-oxoethyl)-phenylamino]-piperidine.

EXAMPLE 29

Cis-3-n-butoxy-3-methyl-4-[(1-oxoethyl)phenylamino]-piperidine

The hydrogenolysis procedure of Example 19 is followed except that an equivalent amount of the cis piperidine obtained in Example 28 is utilized as the starting piperidine to yield as final product, cis-3-n-butoxy-3-methyl-4-[(1-oxoethyl)phenylamino]piperidine.

EXAMPLE 30

Cis-(1-o-methylphenethyl)-3-n-butoxy-3-methyl-4-[(1-oxoethyl)phenylamino]piperidine The alkylation procedure of Example 21 is followed except that an equivalent amount of the cis-piperidine obtained in Example 29 is utilized as the starting piperidine, and an equivalent amount of 2-bromo-1-o-methylphenyl-ethane is used as the alkylating agent in place of 2-bromoethylbenzene, to yield *pas final product, cis-(1 o-methylphenethyl)-3-n-butoxy-3-methyl-4-[(1-oxoethyl)phenylamino]piperidine.

EXAMPLE 31

Cis-N-benzyloxycarbonyl-3-methoxy-3-methyl-4-[(methoxyacetyl)phenylamino]piperidine The acylation procedure of Example 17 is followed except that an equivalent amount of methoxyacetyl chloride is used as the acylating agent in place of propionyl chloride to yield as final product, cis-N-benzyloxycarbonyl-3-methoxy-3-methyl-4-[(methoxyacetyl)-phenylamino]piperidine.

EXAMPLE 32

Cis-3-methoxy-3-methyl-4[(methoxyacetyl)-phenylamino]piperidine

The hydrogenolysis procedure of Example 19 is followed except that an equivalent amount of the cis-piperidine obtained in Example 31 is utilized as the starting piperidine to yield as final product, cis-3-methoxy-3-methyl-4[(methoxyacetyl)phenylamino]-piperidine.

EXAMPLE 33

Cis-3-3-methoxy-3-methyl-4-[(methoxyacetyl)-phenylamino-1-piperidine]propanoic acid, methyl ester The alkylation procedure of Example 21 is followed except that an equivalent amount of the cis-piperidine obtained in Example 32 is utilized as the starting piperidine to yield as final product, Cis-3-[3-methoxy-3-methyl-4-[(methoxyacetyl)phenylamino]-1-piperidine]-propanoic acid, methyl ester.

Example 34

A pharmaceutical composition for parenteral or intravenous analgesic administration can be prepared from the following ingredients:

| Ingredients | Amount |
| --- | --- |
| Cis-3-[3-hydroxy-3-methyl-4-[(1-oxopropyl)phenylamino]-1-piperidine]propanoic acid, methyl ester, HCl salt | 1-10 mg |
| Isotonic saline | 1 liter |

Other compounds of the invention of course can be substituted for the foregoing specific compound, utilizing a relative amount of such other compounds in the composition depending on the effective analgesic activity of the particular compound.

We claim:

1. A method of providing analgesia in a mammal comprising administering to such mammal an analgesically effective amount of a compound having the formula (I):

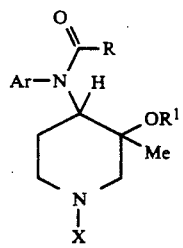

wherein:
X is a member selected from Group I consisting of:
$C_{1-10}$ alkoxy-carbonyl-lower alkyl, lower alkyl-carbonyloxy-lower alkyl,
$C_{1-10}$ alkenyloxy-carbonyl-lower alkyl, and ($C_{1-2}$)alkoxy-($C_{1-2}$)alkoxy carbonyl-lower alkyl;
and from Group II consisting of:
lower alkyl, lower alkenyl, lower alkynyl, thienyl lower alkyl, aryl lower alkyl and (4,5-dihydro-5-oxo-1H-tetrazol-1-yl) lower alkyl which can be substituted in the 4-position with lower alkyl, cyclo($C_{5-6}$) lower alkyl or aryl lower alkyl;
Ar is aryl;
R is a member selected from the group consisting of lower alkyl and lower alkoxy-lower alkyl; and
$R^1$ is a member selected from the group consisting of hydrogen and straight chained lower alkyl;
and the optically active and cis-trans isomers thereof, and the pharmaceutically acceptable acid addition salts of said compounds and isomers.

2. The method of claim 1 wherein X is alkoxy-carbonyl-lower alkyl, R is lower alkyl and $R^1$ is hydrogen.

3. The method of claim 1 wherein X is alkoxy-carbonyl-lower alkyl, R is lower alkyl and $R^1$ is straight chained lower alkyl.

4. The method of claim 1 wherein X is alkoxy-carbonyl-lower alkyl.

5. The method of claim 1 wherein X is methoxy-carbonyl-ethyl.

6. The method of claim 1 wherein R is lower alkyl.

7. The method of claim 1 wherein R is ethyl.

8. The method of claim 1 wherein $R^1$ is hydrogen.

9. The method of claim 1 wherein $R^1$ is straight chained lower alkyl.

10. The method of claim 1 wherein $R^1$ is methyl.

11. The method of claim 1 wherein said compound is selected from the group consisting of:
  a. cis- or trans-3-[3-hydroxy-3-methyl-4[(1-oxopropyl)phenylamino]-1-piperidine]propanoic acid, methyl ester;
  b. cis- or trans-N-[1-(2-thienyl)ethyl]-3-hydroxy-3-methyl-4-[(1-oxopropyl)phenylamino]piperidine; and
  c. cis- or trans-N-phenethyl-3-hydroxy-3-methyl-4-[(1-oxopropyl)phenylamino]piperidine;
and the pharmaceutically acceptable acid addition salts thereof.

12. The method of claim 1 wherein said compound is selected from the group consisting of:
  a. cis- or trans-3-[3-hydroxy-3-methyl-4[(1-oxopropyl)phenylamino]-1-piperidine]propanoic acid, methyl ester;
  b. cis- or trans-N-[1-(2-thienyl)ethyl]-3-hydroxy-3-methyl-4-[(1-oxopropyl)phenylamino]piperidine; and
  c. cis- or trans-N-phenethyl-3-hydroxy-3-methyl-4-[(1-oxopropyl)phenylamino]piperidine;
and the pharmaceutically acceptable acid addition salts thereof.

* * * * *

UNITED STATES PATENT AND TRADEMARK OFFICE
CERTIFICATE OF CORRECTION

PATENT NO. : 5,214,148
DATED : May 25, 1993
INVENTOR(S) : Feldman et al.

It is certified that error appears in the above-identified patent and that said Letters Patent is hereby corrected as shown below:

Title page, item [54] and col. 1, lines 2 and 3:
Please correct the title of the application to read --ANALGESIC N-PHENYL-N-(3-OR[1]-3-Me-4-PIPERIDINYL)AMIDES--.

Title page, item [56] References Cited:
Please correct the prior art reference U.S. Patent No. 4,167,574 to "Janssens" to read --Janssen--.

Please correct the prior art reference US Patent No. 4,962,115 to "Van Daele" to read --van Daele--.

Column 3, lines 16 and 20 change "cis or" to --cis- or--

Column 3, line 59, change "those o formula" to --those formula--.

Column 4, line 48, change "N unsubstituted" to --N-unsubstituted--.

Column 6, line 47, change "N benzyloxycar" to --N-benzyloxycar--.

Column 7, line 44, change "trans-isomers" to --transisomers--.

Column 10, line 2, change "0ºC. to --0ºC--.

Column 11, line 12, change "N-Ethyl 3-OH" to --N-Ethyl-3-OH--.

Column 12, line 45, before "Assay A" please insert

--C. Trans-N-(1-phenethyl)-3-hydroxy-3-methyl-4-[(1-oxopropyl) phenylamino]piperidine oxalate;

D. Cis-3-[3-hydroxy-3-methyl-4-[(1-oxopropyl)phenylamino]-1-piperidine]propanoic acid, methyl ester HCl;

UNITED STATES PATENT AND TRADEMARK OFFICE
CERTIFICATE OF CORRECTION

PATENT NO. : 5,214,148
DATED : May 25, 1993
INVENTOR(S) : Feldman et al.

It is certified that error appears in the above-identified patent and that said Letters Patent is hereby corrected as shown below:

E. Cis-N-[1-(2-thienylethyl)]-3-hydroxy-3-methyl-4-[(1-oxopropyl)phenylamino]piperidine HCl;

F. Trans-3-[3-hydroxy-3-methyl-4-[(1-oxopropyl)phenylamino]-1-piperidine]propanoic acid, methyl ester HCl;

G. Cis-N-(1-phenethyl)-3-methoxy-3-methyl-4-[(1-oxopropyl)phenylamino]piperidine oxalate;

H. Trans-3-[3-methoxy-3-methyl-4-[(1-oxopropyl)phenylamino]-1-piperidine]propanoic acid, methyl ester oxalate;

I. Cis-N-[1-(2-thienylethyl)]-3-methoxy-3-methyl-4-[(1-oxopropyl)phenylamino]piperidine oxalate;

J. Trans-N-[1-(2-thienylethyl)]-3-methoxy-3-methyl-4-[(1-oxopropyl)phenylamino]piperidine oxalate; and K. Trans-N-(1-phenethyl)-3-methoxy-3-methyl-4-[(1-oxopropyl)phenylamino]piperidine HCl.--

Column 13, line 38, change "capsules, pills , powder" to --capsules, pills, powder--

Column 15, line 22, change "(MgSO)4)" to (MgSO4)--.

Column 16, lines 7-11, change formatting to read in paragraph form instead of centered.

Column 16, line 39, change "is lo utilized" to --is utilized--.

Column 16, line 42, change "$C_{19}H_{29}N_2O4Cl:C$" to --$C_{19}H_{29}N_2O_4Cl:C$--.

Column 16, line 29, change "$C_{19}H_{29}N_2O4Cl:C$" to --$C_{19}H_{29}N_2O_4Cl:C$--.

UNITED STATES PATENT AND TRADEMARK OFFICE
CERTIFICATE OF CORRECTION

PATENT NO. : 5,214,148

DATED : May 25, 1993

INVENTOR(S) : Feldman et al.

It is certified that error appears in the above-identified patent and that said Letters Patent is hereby corrected as shown below:

Column 16, line 46, change "4-(1-" to --4-[(1--.

Column 16, line 48, change "[piperidine" to --]piperidine--.

Column 16, line 51, after "(4-", insert --methylphenylsulfonyl) ethanol (376mg, 1.33mmol, 100mol%),--.

Column 16, line 55, change "in 1" to --in 1M--.

Column 16, line 60, change "(MgSo4)" to --(MgSO4)--.

Column 16, line 63, change "3-methyl 4 [(1 oxopropyl)-" to --3-methyl-4-[(1-oxopropyl)---.

Column 17, line 3, change "Trans-N-1-(2" to --Trans-N-[1-(2--.

Column 17, line 14, change "N206" to --N2O6--.

Column 17, line 18, change "Trans-N-phenethyl 3 hydroxy 3-" to --Trans-N-phenethyl-3-hydroxy-3---.

Column 17, line 27, after "suspension" please begin new line at left margin.

Column 17, line 42, change "Cis N-" to --Cis-N---.

Column 17, line 47, change "cis isomer" to --cis-isomer--.

Column 17, line 51, change "anilino 3-methyoxy 3" to --anilino-3-methoxy-3---.

Column 17, line 66, change "trans-N ben-" to --trans-N-ben---.

UNITED STATES PATENT AND TRADEMARK OFFICE
CERTIFICATE OF CORRECTION

PATENT NO. : 5,214,148
DATED : May 25, 1993
INVENTOR(S) : Feldman et al.

It is certified that error appears in the above-identified patent and that said Letters Patent is hereby corrected as shown below:

Column 18, line 3, change "4-anilino" to --4-anilino---.

Column 18, line 4, change "methyl piperidine" to --methyl-piperidine--.

Column 18, line 7, change "cis-N benzloxycarbonyl-4-anilino 3-" to --cis-N-benzloxycarbonyl-4-anilino-3---.

Column 18, line 18, change "7.5 mL)" to (7.5 mL)--.

Column 18, line 25, change "cis-N-benzyloxycarbonyl 3-" to --cis-N-benzyloxycarbonyl-3---.

Column 18, line 26, change "4-[(1 oxopropyl)" to --4-[(1-oxopropyl)--.

Column 18, line 31, change "oxopropyl)phenylamino]" to --oxopropyl)-phenylamino]--.

Column 18, line 38, change "-3 methyl 4" to ---3-methyl-4--.

Column 18, line 39, change "[(1-oxoproyl1phenylamino]" to --[(1-oxopropyl)phenylamino]--.

Column 18, line 51, change "Trans-3-methoxyl-3" to --Trans-3-methoxy-3---.

Column 18, line 65, change "(130 mL)" to (130 µL)--.

Column 19, line 1, change "phenylamino]1-" to --phenylamino]-1---.

Column 19, line 39, change "Trans-N-1-(2" to --Trans-N-[1-(2--.

Column 19, line 54, change "cis 3 methoxy 3 methyl 4 [(1" to --cis-3-methoxy-3-methyl-4-[(1---.

UNITED STATES PATENT AND TRADEMARK OFFICE
CERTIFICATE OF CORRECTION

PATENT NO. : 5,214,148
DATED : May 25, 1993
INVENTOR(S) : Feldman et al.

It is certified that error appears in the above-identified patent and that said Letters Patent is hereby corrected as shown below:

Column 19, line 55, change "150m9" to --150mg--.

Column 19, line 64, change "cis N-" to --cis-N---.

Column 20, line 7, change "-3 methoxy" to --3-methoxy--.

Column 20, line 51, change "cis piper-" to --cis-piper---.

Column 21, line 29, change cis-3-methoxy-3-" to --cis-3-[3-methoxy-3---.

Column 21, line 41, change "Example 34" to --EXAMPLE 34--.

Signed and Sealed this

Twentieth Day of September, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,214,148
DATED : May 25, 1993
INVENTOR(S) : Feldman et al.

It is certified that error appears in the above-indentified patent and that said Letters Patent is hereby corrected as shown below:

Col. 12 line 33, change ."of limited the invention" to "of limiting the invention".

Col. 13 line 38, change "capsules, pills, powder" to "capsules, pills, powder"

Col. 13 line 40, change "teaspoonfuls" to "teaspoonsful".

Signed and Sealed this

Twentieth Day of December, 1994

Attest:

BRUCE LEHMAN

*Attesting Officer*  *Commissioner of Patents and Trademarks*